United States Patent [19]
Laniado et al.

[11] Patent Number: 5,873,369
[45] Date of Patent: Feb. 23, 1999

[54] SYSTEM FOR MONITORING HEALTH CONDITIONS OF AN INDIVIDUAL AND A METHOD THEREOF

[75] Inventors: Shlomo Laniado, Tel-Aviv; Naftali Stern, Moshav Nir Tzvi; Arie Roth, Tel-Aviv, all of Israel

[73] Assignee: Chronoslim P.C.E. Ltd., Netanya, Israel

[21] Appl. No.: 828,590

[22] Filed: Mar. 31, 1997

[51] Int. Cl.⁶ ...................................................... A61B 5/00
[52] U.S. Cl. ........................................... 128/903; 600/300
[58] Field of Search ..................... 128/903, 904; 600/300, 490, 494–7, 500, 503

[56] References Cited

U.S. PATENT DOCUMENTS

| | | | |
|---|---|---|---|
| 5,007,429 | 4/1991 | Treatch et al. ........................... | 600/490 |
| 5,228,449 | 7/1993 | Christ et al. ............................ | 600/503 |
| 5,335,664 | 8/1994 | Nagashima . | |
| 5,339,821 | 8/1994 | Fujimoto . | |
| 5,544,661 | 8/1996 | Davis et al. . | |
| 5,576,952 | 11/1996 | Stutman et al. ......................... | 600/300 |
| 5,579,378 | 11/1996 | Arlinghaus, Jr. ........................ | 128/904 |
| 5,614,887 | 3/1997 | Buchbinder ............................. | 600/300 |
| 5,628,324 | 5/1997 | Sarbach . | |
| 5,718,235 | 2/1998 | Golosarsky et al. . | |

*Primary Examiner*—Robert L. Nasser
*Attorney, Agent, or Firm*—Browdy and Neimark

[57] ABSTRACT

A method and system for monitoring a health condition of an individual. At least one physiological parameter of the individual is measured and measured data is then processed in order to detect a potential danger in the measured parameter. Upon detecting the potential danger, a warning signal representative of the potential danger is generated, and a signal for indicating to the individual to actuate a personal communication unit is provided during a predetermined period of time. Upon actuating the personal communication unit, an information message representative of the warning signal is transmitted to the individual. In the absence of actuating the personal communication unit during the predetermined period of time, data indicative of the warning signal is transmitted to a central monitoring station.

19 Claims, 5 Drawing Sheets

SYSTEM FOR MONITORING HEALTH CONDITIONS OF AN INDIVIDUAL AND A METHOD THEREOF

FIELD OF THE INVENTION

The present invention relates to a method and system for monitoring a health condition of an individual, in particular his heart condition.

BACKGROUND OF THE INVENTION

Patients suffering from chronic diseases, particularly cardiovascular diseases, should continuously or periodically be monitored by medical specialists to stave off danger of death. Needless to say, reaction time to cardiovascular changes of cardiac patients is a very important, and, even, determinant, factor in effective prevention of fatal attack.

There is a great variety of systems having a common goal of immediately detecting danger of health conditions of a patient and notifying a clinician without any action on the part of the patient. Such a system is disclosed in U.S. Pat. No. 5,339,821, which relates to a home medical system and a medical apparatus for use therewith by which a patient having a disease or a healthy person can measure the daily condition of the disease, or the condition of health, at home. The system thus enables the patient to check certain physiological parameters, such as blood pressure and pulse, by following on-line instructions coming from a medical specialist at central medical station site.

U.S. Pat. No. 5,544,661 discloses a portable device attached to a patient and a central monitoring station. The portable device typically provides access to one or more physiological parameters of the patient and transmits them to a clinician at the central monitoring station, when emergency attention is required. The clinician has both voice contact with the patient and access to interventional therapeutic devices attached to the patient.

Hence, in both of the above examples, continuous direct interaction between the patient and the clinician is required during the monitoring process. However, it is often the case that an individual, either suffering from disease, in particular heart disease, or not, needs to check his health condition. If it appears that the individual is sufficiently well and does not need emergency assistance, communication with a clinician at a central monitoring station is clearly unnecessary. On the other hand, if either a dangerous situation really occurs, or the individual himself feels need for assistance, immediate contact with medical specialists must be made.

SUMMARY OF THE INVENTION

It is an object of the present invention to provide a method and system for monitoring a health condition of an individual, in which a central monitoring and supervision station is accessed only in case of actual or potential danger in the health condition of the individual.

It is a further object of the present invention to provide such a method and a system, wherein the individual is afforded a measure of control as to whether or not to access the central monitoring station.

Thus provided according to one aspect of the invention is a method for monitoring a health condition of an individual comprising the steps of:

(a) measuring at least one physiological parameter of the individual and generating data representative of said at least one measured parameter;

(b) processing the data to detect a potential danger in said at least one measured parameter;

(c) upon detecting the potential danger:
  (i) generating a warning signal representative of the potential danger;
  (ii) providing, during a predetermined period of time, a signal for indicating to the individual to actuate a personal communication means thereof;

(d) upon actuating the personal communication means, transmitting an information message to the individual representative of said warning signal; and (e) in the absence of actuating the personal communication means during said predetermined period of time, transmitting data indicative of the warning signal to a central monitoring station.

In order to detect the potential danger in the physiological parameter, the measured data may be compared to a corresponding reference value.

Preferably, upon receiving the information message representative of the warning signal, the individual can either initiate contact with the central monitoring station, or cancel the warning signal. Upon receiving the information message, which may be vocal or displayed, the individual may store the warning signal to keep a record thereof.

According to another aspect of the present invention there is provided a system for monitoring a health condition of an individual, the system comprising:

measuring means for attaching to the individual to measure at least one physiological parameter thereof and for generating data representative of said at least one measured parameter;

processing means coupled to the measuring means for measuring the data representative of said at least one measured parameter so as to determine whether said parameter is indicative of a potential danger condition and, if so, generating a corresponding warning signal; and a personal communication means of the individual, including:
  indication means responsive to the warning signal for providing, for a predetermined period of time, an indicating signal;
  message generating means for receiving the warning signal and generating an information message representative thereof;
  acknowledgement means operative by the individual for acknowledging receipt of the indication signal and producing an acknowledgment signal;
  access request means being either manually operated by the individual or being actuated automatically in the absence of said manual operation a predetermined period of time after receiving said warning signal for transmitting data indicative of the warning signal to a central monitoring station; and
  access request disabling means coupled to the access request means and to the acknowledgment means and responsive to the acknowledgement signal for disabling automatic operation of the access request means.

The measuring means preferably includes infra-red and other electronic transducers. The processing means may comprise a first memory for storing a reference value for the physiological parameter to be measured; a second memory for storing the warning signal; and a self-programming means coupled to the first and second memories, and to the personal communication means of the individual, for comparing the data representative of the measured parameter to the corresponding reference value and, upon detecting the danger condition, simultaneously actuating the indication means and the delay means.

The access request means may be programmed for automatically dialing a phone number of the central monitoring station, and transmitting a signal representative of an identification code of the individual together with the warning signal.

The measuring means and processing means are preferably accommodated within a single unit in the form of a wristwatch, while the personal communication means is preferably a cellular telephone of a small size.

The present invention may be used for monitoring various physiological parameters of the individual, such as pulse rate, temperature, blood pressure and blood oxygen saturation. More specifically, the invention is used for monitoring pulse rate and indicating of sudden variations thereof and is, therefore, described below with respect to this application.

BRIEF DESCRIPTION OF THE DRAWINGS

These and further constructional features and advantages of the invention will be better appreciated in the light of the ensuing description of a preferred embodiment thereof, given by way of example only, with reference to the accompanying drawings, in which:

FIG. 4 is a flow diagram illustrating the principal steps for operating the processor shown in FIG. 3a.

DETAILED DESCRIPTION OF THE PREFERRED EMBODIMENT

Figure 1:
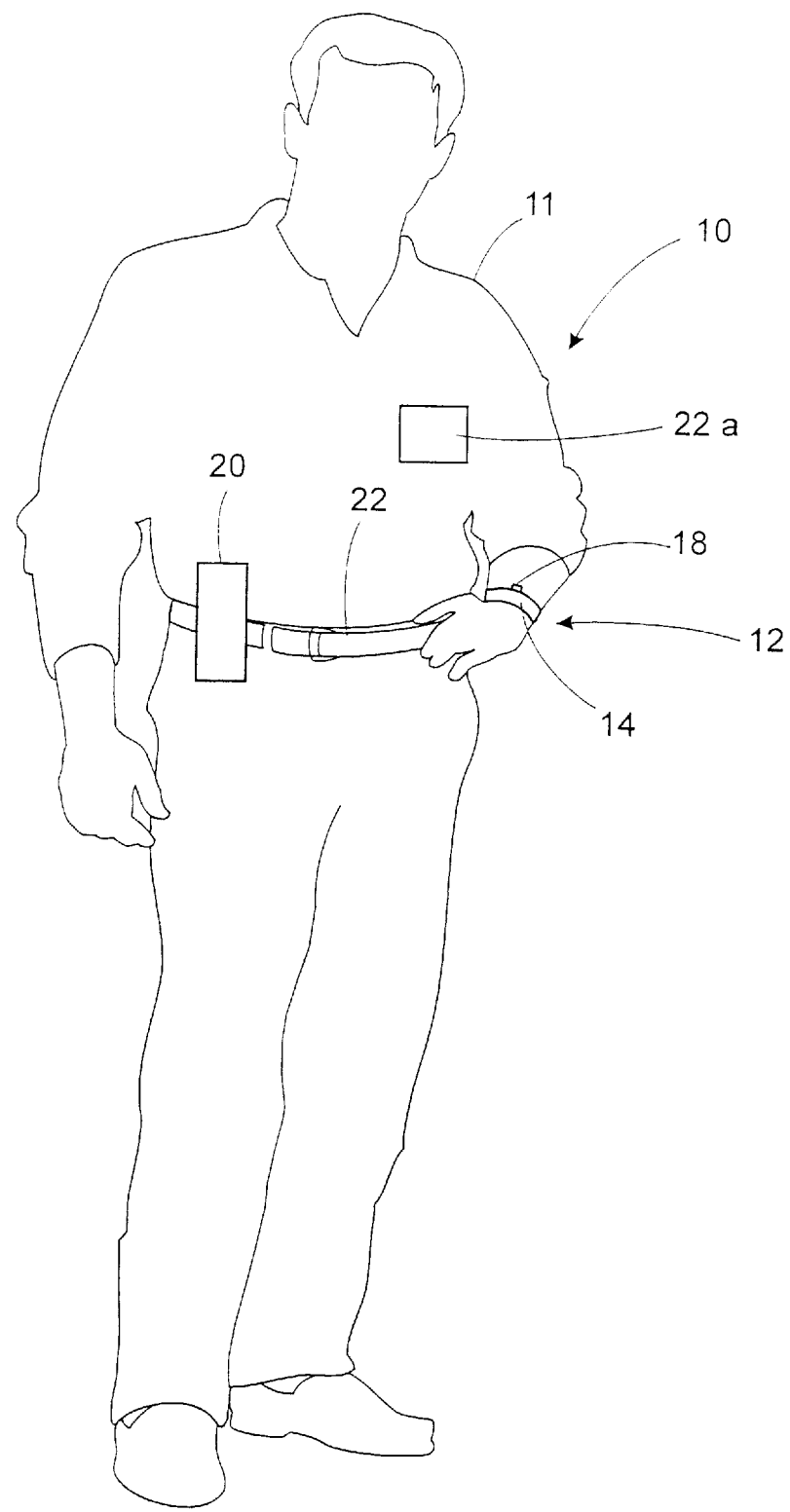
FIG. 1 is a pictorial representation of a system according to the invention, worn by an individual.

Referring to FIG. 1, there is illustrated a system, generally denoted 10, which is worn by an individual 11 for monitoring his pulse rate. The system 10 comprises a portable unit, generally at 12, which is in the form of a wristwatch having a conventional strap 14 for overlying a region of the individual's wrist around his radial artery. The individual 11 can switch on the system 10 by pressing a push-button 18 appropriately accommodated on the wristwatch 12. A conventional cellular phone 20 (constituting a personal communication means) is supported on a waist-belt 22 worn by the individual 11. Alternatively, although not specifically shown, the cellular phone 20 may be carried within a pocket and, preferably, a shirt pocket 22a of the individual. The cellular phone 20 allows the individual 11 to communicate with a central monitoring station through a communication link, and typically comprises either a phone receiver or a call button, which is not specifically shown.

Figure 2:
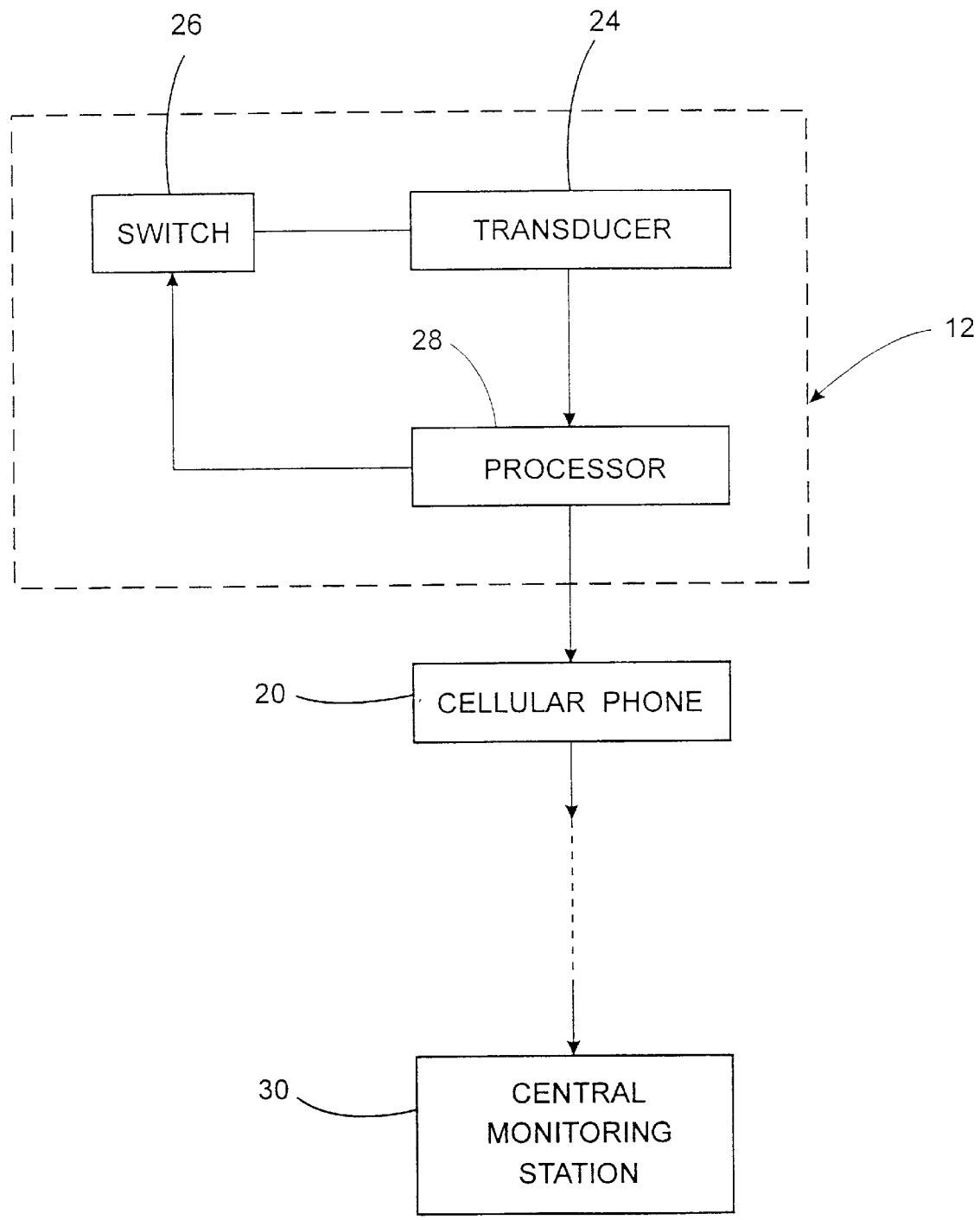
FIG. 2 is a block diagram showing the principal components of the system of FIG. 1.

FIG. 2 shows the principal components in the system 10. A suitable transducer 24 is provided and actuated by a switch means 26 in a conventional manner for sensing the individual's pulse rate. The construction and operation of the transducer 24 do not form the part of the present invention and therefore are not be described in detail, except to note that it is located on or around the individual's radial artery being suitably accommodated within the strap 14. Coupled to the transducer 24 is a processor 28, which is, in turn, wireless coupled to the cellular phone 20, the details of which will be described further below with reference to FIG. 3b. The central monitoring station 30 to which the cellular phone 20 is coupled may be of known type and is, therefore, not specifically described. It should be noted that the transducer 24 can be switched on/off either manually by pressing the button 18, or automatically by the processor 28.

Figure 3A:
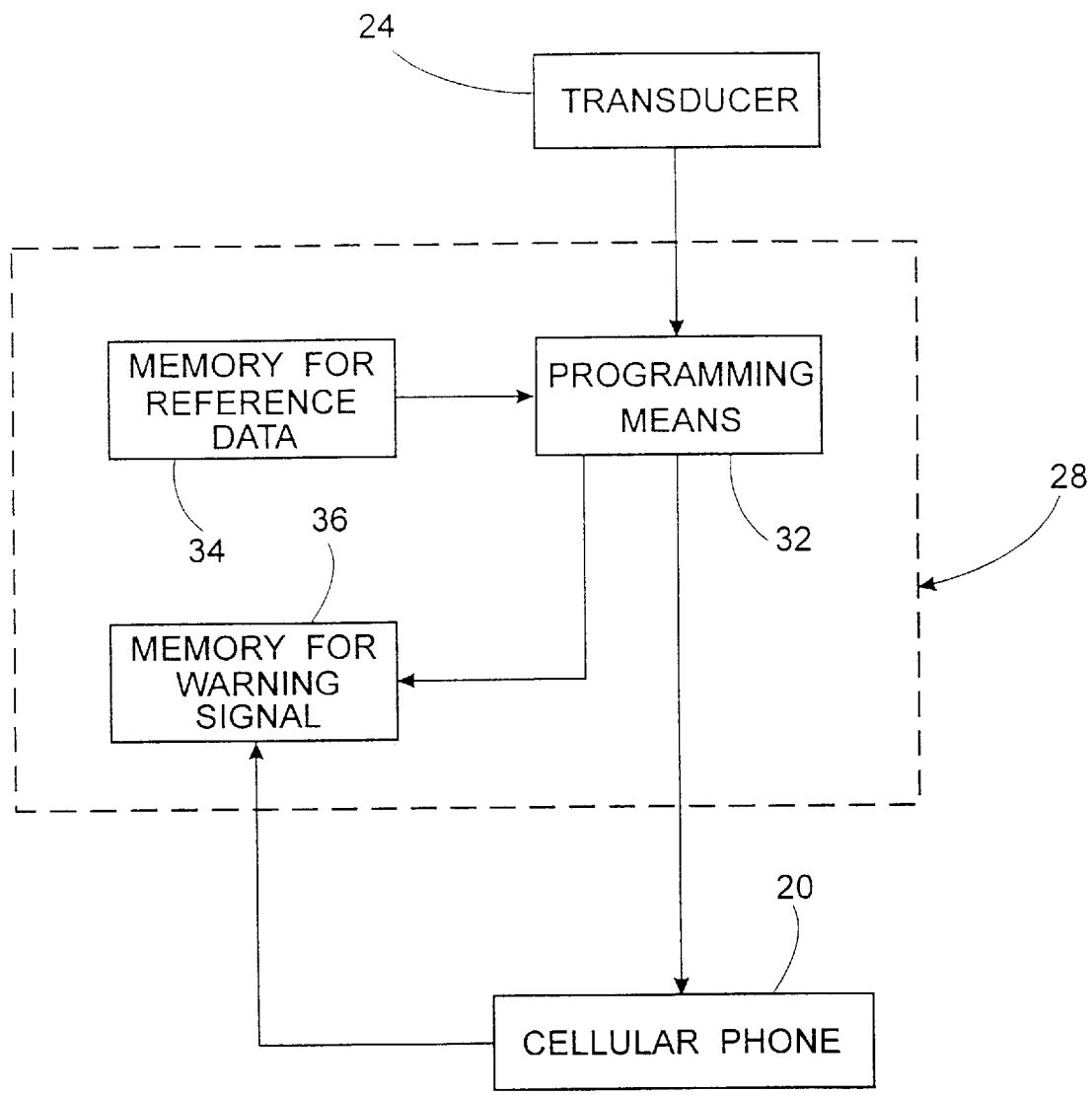
FIG. 3a is a block diagram showing a detail of a processor for use with the system of FIG. 2.

Turning now to FIG. 3a, there are functionally illustrated the main assemblies of the processor 28. Thus, the processor 28 includes a programming means 32 directly interconnected between the transducer 24 and the cellular phone 20, in a manner to receive data representative of the pulse rate measured by the transducer 24, process the received data and transmit the processed data to the cellular phone 20. Coupled to the programming means 32 is a memory 34 for storing previously inputted reference data, namely the allowed limits for the pulse rate of the individual. Further coupled to the programming means 32 is a memory 36 for storing the processed data.

It will be thus readily understood that the main functions of the programming means 32 are as follows:

1) receiving from the transducer 24 data representative of the measured value of the pulse rate;

2) comparing the received value to the reference value stored in the memory 34;

3) if the received value is within the allowed limits, allowing the transducer 24 to continue sensing the pulse rate; if the measured value appears to be out of its allowed limits, generating a respective warning signal representative of comparison analysis; and 4) transmitting the warning signal to the personal cellular phone 20, and automatically storing the warning signal in the memory 36 to keep a record thereof.

The warning signal generated by the programming means 32 for inputting the cellular phone 20 is thus in the form of a radio signal, and the system 10, therefore, further includes a conventional antenna, which is not specifically shown.

Figure 3B:
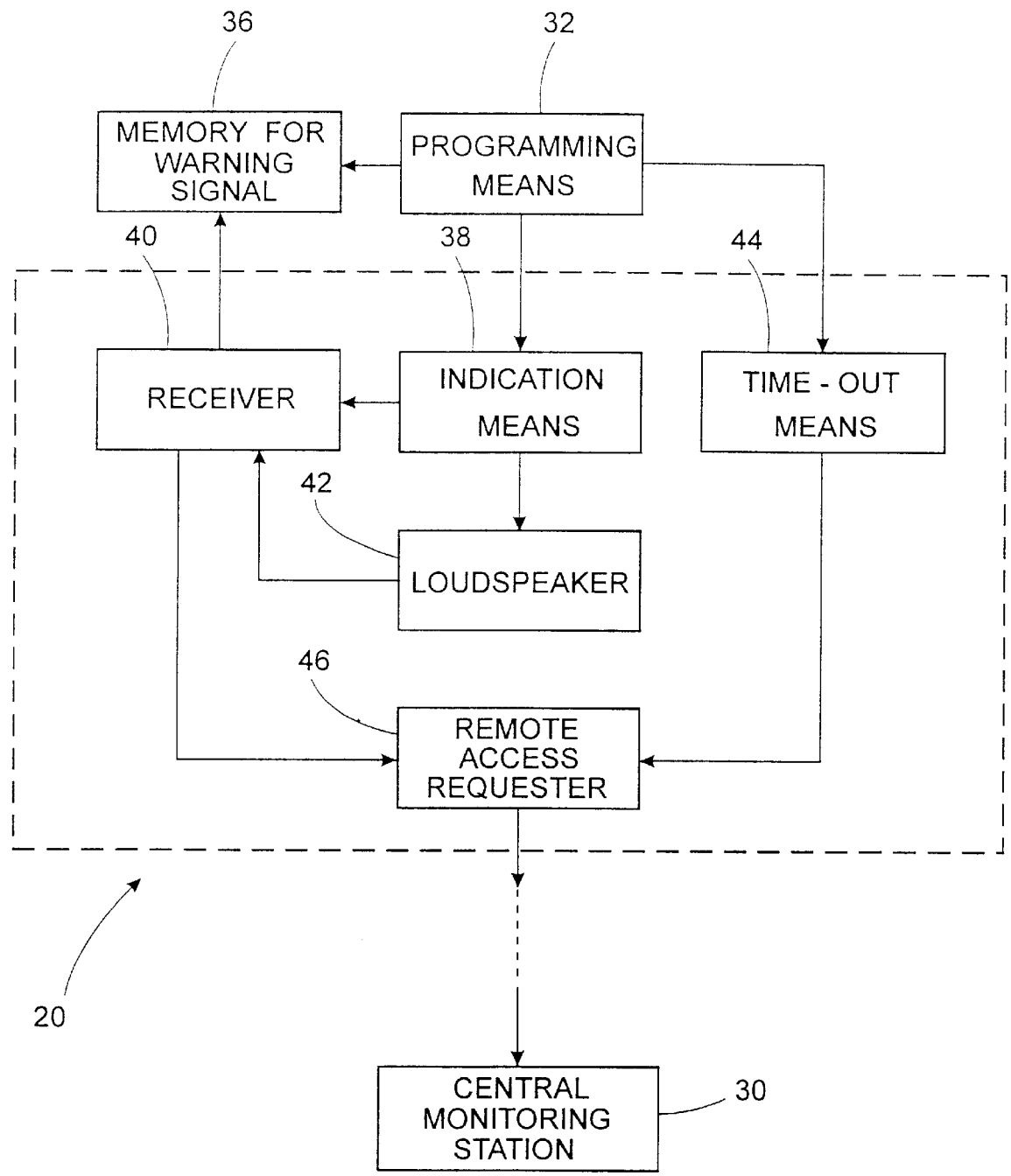
FIG. 3b is a block diagram more specifically illustrating a personal communication unit of the system of FIG. 2.

FIG. 3b shows functionally the main components of the personal cellular phone 20. An indication means 38 is provided and connected to the programming means 32 so as to be actuated by the warning signal and generate an indication signal for the individual 11, for example a sound signal. Coupled to the indication means 38 in a conventional manner is a receiver 40 having a speaker 42 for producing a vocal message representative of the comparison analysis. All these components are well known per se and need not be specifically described.

Further provided is a conventional time-out unit 44 connected to the programming means so as to be fed by the warning signal, and typically programmed to delay the output of the warning signal for a preset period of time. It will be appreciated, that the time-out unit being a part of the cellular phone 20 operates similar to a conventional automatic answering machine which typically comprises a self-programming means for providing a certain outgoing message after a preset number of phone rings, which outgoing message is the warning signal coming from the programming means 32, in the present example.

The phone unit 20 further includes an access requester 46 coupled both to the receiver 40 and to the time-out unit 44 so as to be selectively actuated either manually by the receiver, or automatically by the warning signal coming from the time-out unit 44. The access requester 46 is in the form of a keypad usually employed in conventional cellular phones and can additionally comprise an automatic dialing mode. As is known, the automatic dialing mode is a quick and convenient way of dialing which is done by a speed dial key actuated either manually or automatically. To use automatic dialing mode, the phone number of the central monitoring station 30 should be previously stored in a memory of the cellular phone.

Thus, the access requester 46 keeps in its memory a record of the individual's identification code together with the phone number of the central monitoring station, and, when actuated, transmits the identification code of the individual together with the warning signal, received from either the receiver 40 or the time-out means 44, to the central monitoring station 30 through a communication link. The communication link thus provides a data channel (not shown) over which the warning signal can be transferred from the cellular phone 20 to the station 30, and allows for direct voice interaction between the clinician at the central station and the individual 11.

It is appreciated that means are provided at the central monitoring station to indicate to the medical specialists where the warning signal comes from, namely from the time-out unit 44 which represents the more dangerous situation implying that the individual is not in a position to make interventional action, or from the receiver 40 which enables the specialist to speak to the individual. To this end, either separate receiving links are provided at the station 30, or the access requester 46 is additionally programmed for adding to the warning signal a respective code depending on how the requester 46 is actuated, i.e. via the receiver 40 or the time-out unit 44.

Figure 4:
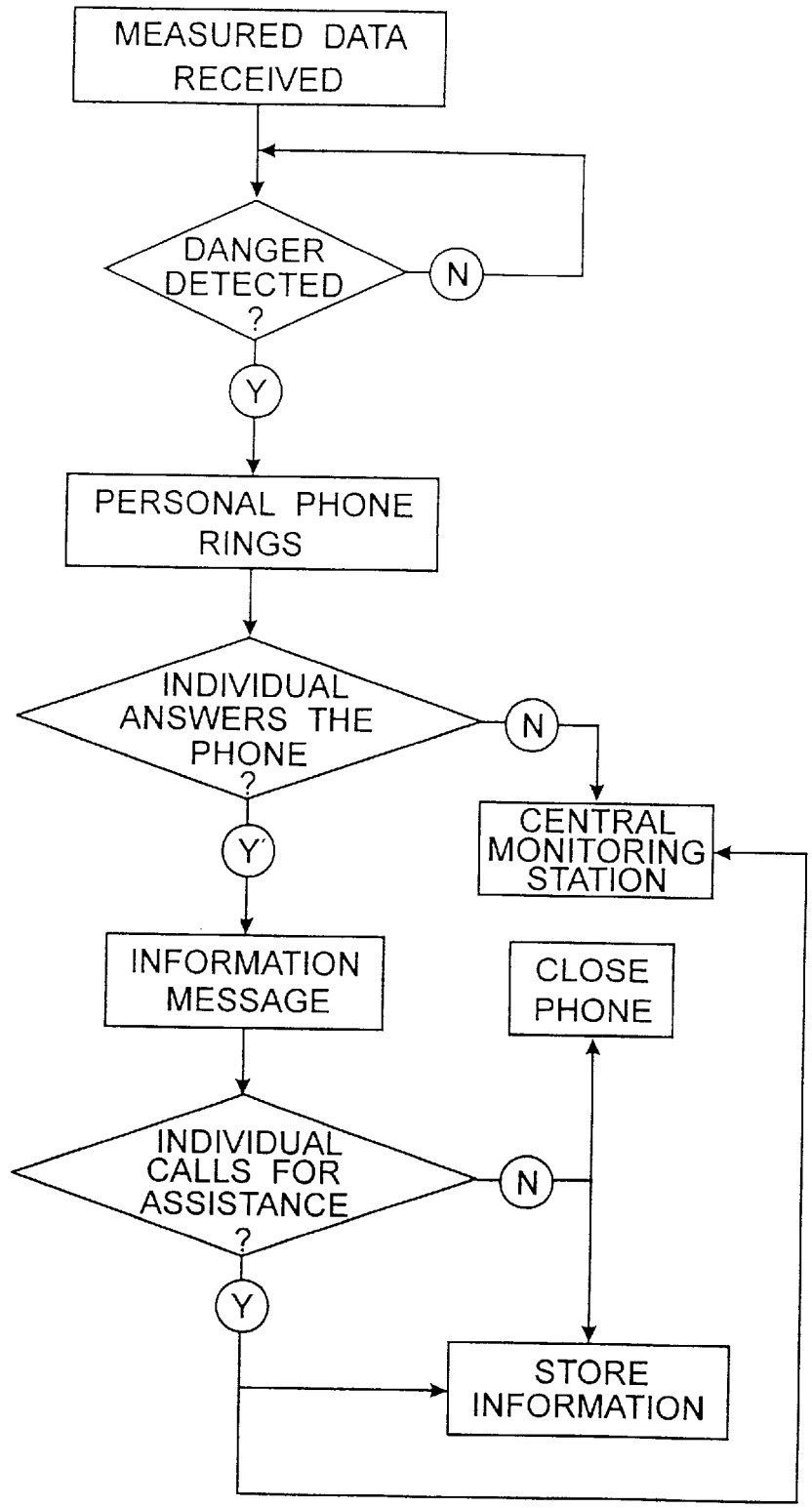

Reference is now made to FIG. 4, illustrating a flow diagram of the principal steps of operation of the system 10. Initially, the pulse rate of the individual 11 is measured by the transducer 24. Measured data is then processed by the processor 28 in the manner described above so as to determine whether the pulse rate of the individual is out of the allowed limits representing a potential danger to the individual's life. Thus, the pulse rate of the individual is continuously measured and processed until a danger condition occurs. When such danger condition is detected, his personal cellular phone 20 starts to ring to call the individual's attention to immediately answer the phone. If the individual is sufficiently well and alert to answer the phone as described above, then the speaker 42 presents the vocal message reporting the dangerous situation. Depending on the gravity of the situation, the individual may also be recommended to contact medical specialists at the central monitoring station without delay and, if driving a vehicle, to stop as soon as possible.

Hence, the individual himself, on the basis of received data, has to decide whether or not he needs to contact the monitoring center 30. In a preferred embodiment, he has the following two options. He can relate to the warning as being erroneous, in which case he can simply cancel the warning and stop its transmission to the central monitoring station for example by closing the phone. Alternatively, the individual can accept the accuracy of the vocal information as a danger alert and transmitted to the monitoring center in a manner as previously described.

In another embodiment in which the warning system is not automatically stored, the individual has three options, including the two mentioned above and simple storage of the warning message in the memory 36 to keep a record thereof. For example, he might be running up a steep flight of stairs and receive the vocal message "YOUR PULSE HAS RISEN TO 120", which may be completely compatible with that activity. In this case, he can again choose either to cancel, or, possibly, to store the warning message in the memory 36 of the processor 28 so as to keep a record thereof. The third possibility is that the individual accepts the warning as a danger alert and allows the warning signal to be automatically relayed to the monitoring center in a manner as previously described. In the event that the individual does not answer his phone means during the predetermined period of time, the warning signal is automatically transmitted to the monitoring center to notify medical personnel.

Those skilled in the art will readily appreciate that many variations, modifications and changes may be applied to the invention as exemplified without departing from its scope as defined in and by the appended claims. Thus, for example, the wristwatch 44 may be designed for detecting arrhythmia by providing additional transducer means for analyzing the individual's heartbeat, and/or for detecting changes in blood pressure, and/or temperature, and/or blood oxygen content, or the like. Furthermore, the wristwatch 44 may comprise a liquid crystal display for displaying an information representative of the warning signal. Additionally, it may have conventional clock mechanism with a clock-face.

What is claimed is:

1. A method for monitoring a health condition of an individual comprising the steps of:
  (a) measuring at least one physiological parameter of the individual and generating measured data representative of said at least one measured parameter;
  (b) processing the measured data to detect a potential danger in said at least one parameter;
  (c) upon detecting the potential danger:
    (i) generating a warning signal representative of the potential danger;
    (ii) providing an indication signal for indicating to the individual to actuate a personal communication device thereof;
  (d) if the individual actuates the personal communication device within a predetermined period of time, transmitting an information message representative of said warning signal to the individual;
  (e) if the individual does not actuate the personal communication device during said predetermined period of time, transmitting data indicative of the warning signal to a central monitoring station.

2. The method according to claim 1, wherein said processing of the measured data includes analyzing the measured data in view of predetermined reference data.

3. The method according to claim 1, further comprising the step of:
  upon receipt of the information message representative of said warning signal by the individual, initiating a contact with the central monitoring station.

4. The method according to claim 1, and also comprising the step of:
  upon receipt of the information message by the individual, cancelling the warning signal.

5. The method according to claim 1, wherein said information message is a vocal.

6. The method according to claim 1, wherein said at least one physiological parameter is pulse rate.

7. The method according to claim 1, wherein said at least one physiological parameter is temperature.

8. The method according to claim 1, wherein said at least one physiological parameter is blood pressure.

9. The method according to claim 1, wherein said at least one physiological parameter is blood oxygen saturation.

10. The method according to claim 1 further comprising the step of:

upon detecting the potential danger, automatically storing the warning signal to keep a record thereof.

11. A system for monitoring a health condition of an individual, the system comprising:

measuring means for attaching to the individual to measure at least one physiological parameter thereof and to generate measured data representative of said at least one parameter;

processing means coupled to the measuring means for processing the measured data so as to determine whether said measured data is indicative of a potential danger condition and, if so, generating a corresponding warning signal; and a personal communication device which is accommodated in the vicinity of the individual and is wireless coupled to the measuring unit, the personal communication device including:

indication means responsive to the warning signal for providing an indication signal;

time-out utility responsive to the warning signal so as to delay its transmission for a predetermined period of time;

message generating means for receiving the warning signal and generating an information message representative thereof;

receiver/transmitter means coupled to the message generating means and capable of, when actuated by the individual, transmitting the information message to the individual, and, when operated by the individual, allowing the warning signal to be transmitted to a central monitoring station, thereby acknowledging the receipt of the indication signal by the individual;

access request means coupled to the receiver/transmitter means and to the time-out utility, so as to be either operated by the individual or be actuated by the time-out utility for automatically transmitting the warning signal to a central monitoring station after said predetermined period of time expires.

12. The system according to claim 11, wherein the processing means comprises:

a first memory for storing reference data associated with said at least one physiological parameter;

a second memory for storing a record representative of the warning signal; and self-programming means coupled to the first and second memory, and to the personal communication means of the individual, for analyzing the measured data in view of the corresponding reference data and, upon detecting the danger condition, generating and storing said record and actuating the indication means and the time-out utility.

13. The system according to claim 11, wherein said measuring means and processing means are accommodated within a single unit adapted for wearing on a wrist of the individual.

14. The system according to claim 11, wherein said personal communication device is a portable telephone.

15. The system according to claim 14, wherein the warning signal generated by the processing means is in the form of a radio signal.

16. The system according to claim 11, wherein said at least one physiological parameter is a pulse rate.

17. The system according to claim 11, wherein said at least one physiological parameter is a temperature.

18. The system according to claim 11, wherein said at least one physiological parameter is a blood pressure.

19. The system according to claim 11, wherein said at least one physiological parameter is a blood oxygen saturation.

* * * * *